United States Patent [19]

Chatterjee

[11] Patent Number: 5,047,342
[45] Date of Patent: Sep. 10, 1991

[54] CLONING AND EXPRESSION OF T5 DNA POLYMERASE

[75] Inventor: Deb K. Chatterjee, Gaithersburg, Md.

[73] Assignee: Life Technologies, Inc., Gaithersburg, Md.

[21] Appl. No.: 391,930

[22] Filed: Aug. 10, 1989

[51] Int. Cl.[5] .......................... C12N 9/12; C12N 1/20; C07H 15/12; C07H 19/06

[52] U.S. Cl. .................... 435/194; 435/239; 435/252.3; 435/252.33; 435/320.1; 435/172.3; 536/26; 536/27; 536/28; 536/29; 530/826

[58] Field of Search ................. 536/28, 27, 29; 435/6, 435/239, 252.3, 252.33, 320, 68, 172.3, 320, 194; 530/826

[56] References Cited

U.S. PATENT DOCUMENTS

| 4,689,406 | 8/1987 | Banks et al. | 435/172.3 |
| 4,766,066 | 8/1988 | Kunstoss et al. | 435/91 |
| 4,795,699 | 1/1989 | Tabor et al. | 435/803 |

FOREIGN PATENT DOCUMENTS

| 0265293 | 4/1988 | European Pat. Off. | 435/194 |
| WO89/06691 | 7/1989 | PCT Int'l Appl. | 435/194 |

OTHER PUBLICATIONS

A copy of the European Search Report cited in corresponding European Patent Application No. 90308751.8.

Das et al., *J. Carbohydr. Nucleosides, Nucleotides,* 5(5):457–67, (1979).
Bernad et al., *Cell,* 59:219–228, (1989).
Fujimura et al., *the Journal of Biological Chemistry,* 251(7):2168–2175, (1976).
Leavitt et al., *Proc. Natl. Acad. Sci. USA,* 86:4465–4469, (1989).
Lin et al., *Proc. Natl. Acad. Sci. USA,* 84:7000–7004, (1987).
Minkley et al., *The Journal of Biological Chemistry,* 259(16):10386–10392, (1984).
Fujimura et al., *J. Virol.,* 53(2):495–500, (1985).
Remaut et al., *Gene,* 15:81–93, (1981).
Shibui et al., *Agric. Biol. Chem.,* 52(4):983–988, (1988).
Stueber et al., *Embo J.,* 3(13):3143–3148, (1984).

*Primary Examiner*—Robert A. Wax
*Assistant Examiner*—Stephanie W. Zitomer
*Attorney, Agent, or Firm*—Sterne, Kessler, Goldstein & Fox

[57] ABSTRACT

The present invention discloses a recombinant DNA molecule having a structural gene encoding a processive, thioredoxin-independent DNA polymerase, a promoter, and an origin of replication. The protein may also have a processive 3'-to-5' DNA exonuclease activity. A method for producing this enzyme is also disclosed, as is the protein produced by this process. This invention is exemplified by expression of T5 DNA polymerase in *E. coli.*

20 Claims, 3 Drawing Sheets

LEAVITT AND ITO

METTyrSerIleCysValThrArgSerCysProValValCysSerLysLysHisIleThr...
...ATGTATTCCATATGTGTAACGAGAAGTTGTCCGGTCGTTGCTCAAAAAGCATATTACT...
+1      +        +        +        +        +        +60
...ATGTATTCCATATGTAACGAGAAGTTGTCCGGTCGTTGCTC-AAAAAGCATATTACT...
    METCysAsnGluLysLeuSerGlyArgLeuLeu-LysLysHisIleThr...

CORRECTED SEQUENCE

FIG. 1

CLONING AND EXPRESSION OF T5 DNA POLYMERASE

FIELD OF THE INVENTION

This invention relates to molecular cloning and expression of the DNA polymerase of the *E. coli* bacteriophage T5.

BACKGROUND OF THE INVENTION

DNA polymerases synthesize the formation of DNA molecules from deoxynucleoside triphosphates using a complementary or template DNA strand and a primer. DNA polymerases synthesize DNA in the 5' to 3' direction by successively adding nucleotides to the free 3' hydroxyl group of the growing strand. The template strand determines the order of addition of nucleotides via Watson-Crik base pairing. In the cell, the DNA polymerase is involved in repair synthesis and DNA replication.

Bacteriophage T5 induces the synthesis of a phage DNA polymerase upon infection of its host *Escherichia coli*. The T5 DNA polymerase (T5-DNAP) was purified to homogeneity by Fujimura and Roop as reported in *J. Biol. Chem.* 25:2168–2175 (1976). Fujimura et al. also disclosed in *J. Virol.* 53:495–500 (1985) the approximate location of T5-DNAP on the physical restriction enzyme map generated by Rhoades (*J. Virol.* 43:566–573 (1982)).

In molecular biology, DNA polymerases have several uses. In cloning and expression experiments, DNA polymerases are used to produce the heterologous polypeptide from the cloned gene. DNA polymerases with exonuclease activity are used in the nick-translation technique for labelling DNA in vitro. Recently, DNA polymerases have been used for DNA sequencing. Tabor and Richardson, U.S. Pat. No. 4,795,699, disclose that processive, host thioredoxin-requiring, T7-type DNA polymerases, especially those lacking substantial exonuclease activity, are very useful for DNA sequencing.

SUMMARY OF THE INVENTION

The DNA polymerase of E. coli bacteriophage T5 is distinguished from other DNA polymerases by its high degree of processivity. In other words, a particular T5-DNAP molecule will replicate a single template DNA molecule without dissociation. Das and Fujimura, *J. Biol. Chem.* 252:8700–8707 (197 ), and Das and Fujimura, *J. Biol. Chem.* 254:1227–1232 (1979), report that T5-DNAP processively synthesizes about 140 to about 200 nucleotides before dissociation. In contrast, other DNA polymerases, such as T4 DNA polymerase, Klenow, and reverse transcriptase, tend to dissociate from the template/newly synthesized strand duplex after only a few bases: a newly synthesized strand will usually have been synthesized by several different enzyme molecules. Similarly, the 3'-to-5' exonuclease activity of T5-DNAP is highly processive; a particular DNA strand will usually be hydrolyzed by only one exonuclease molecule. T5-DNAP is also exceptionally good at displacing nicked duplex DNA strands while synthesizing a new strand. Most DNA polymerases need other protein factors or enzymatic activities (e.g. 5'-to-3' exonuclease) to accomplish the same result.

These strand displacement and processivity qualities make T5-DNAP a good polymerase to use for DNA sequencing or in a DNA amplification scheme. T5-DNAP does not need a protein co-factor to be active or processive, in contrast to other polymerases useful for the same biochemical tasks. For example, T7 DNA polymerase, which also processive and often used for DNA sequencing, needs *E. coli* thioredoxin as a cofactor. Lastly, in infections of *E. coli* by T5 phage, T5-DNAP is present at very low levels, which increases production costs in using the T5-DNAP. To date, this has made commercial production impractical because acceptable, though less effective, alternatives are available at more reasonable costs. Therefore, it is an object of the present invention to provide improved means for producing T5 DNA polymerase. The 3'-to-5' exonuclease activity of many DNA polymerases is disadvantageous in situations where one is trying to achieve net synthesis of DNA. Therefore it is another object of the present invention to provide a T5-DNAP derivative lacking this exonuclease activity.

The present invention is predicated on several discoveries. Fujimura et al. showed that the gene for T5-DNAP is on the SmaI fragment D. Using this information, it should have been possible to clone the gene using a simple, straight-forward cloning strategy. However, it was discovered that due to the presence of sequences near the T5-DNAP gene deleterious to the host cell that the gene could not be directly cloned. In order to clone the T5-DNAP gene, the deleterious T5 sequences flanking the T5-DNAP gene, in particular sequences 5'-to the structural gene, must be removed before it can be cloned in an *E. coli* host cell.

Leavitt & Ito, *Proc. Nat'l Acad. Sci. U.S.A.* 86:4455–4469 (1989) disclosed the cloning of fragments of the T5-DNAP gene the sequencing thereof. These fragments were not reassembled, nor was expression of the gene obtained. Further, the published sequence of Leavitt & Ito is incorrect at its 5'-end (see FIG. 1). Specifically, an extra "A" residue is reported in the region of nucleotides +45 to +50. This mistake corrupts the open reading frame analysis, leading to an improperly derived sequence for the amino-terminus of the protein, substituting an improper polypeptide of 15 amino acid residues for the correct 11 residue sequence. Use of this sequence to engineer the T5-DNAP gene would leave excess flanking sequences at the 5'-end, which can lower expression levels. Specifically, it has been discovered that with a construction that places a heterologous ribosome binding site immediately next to the translational initiation codon will produce higher levels of enzyme than constructions that are identical except for the retention of small amounts of 5'-flanking sequences. Furthermore, use of the published sequence from Leavitt & Ito, in some types of constructions, can lead to translational initiation out of the correct reading frame. For example, a fusion protein initiating 5'-to the sequencing error disclosed in FIG. 1 would be unexpectedly inoperative. Given the herein disclosed teachings, detailed in the Examples, one of ordinary skill in the art can use standard recombinant DNA techniques to practice the preferred embodiments, namely expression of T5 DNA polymerase in *E. coli*.

BRIEF DESCRIPTION OF THE DRAWING

FIG. 1 is a comparison of the sequences disclosed herein with those published by Leavitt & Ito, *Proc. Nat'l Acad. Sci. USA* 86:4465–4469 (1989). The upper half of FIG. 1 gives Leavitt & Ito's DNA sequence and the protein sequence derived therefrom. The lower half of the Figure gives a corrected DNA sequence and a corrected protein sequence derived therefrom. The numbering convention is as in Leavitt & Ito. The "AUG" translational start codons are in bold letters, as is the location of extra "A" introduced into the sequence. Note that the exact location of the mistake could be anywhere in the string of "A"s.

DETAILED DESCRIPTION OF THE INVENTION

Figure 2:
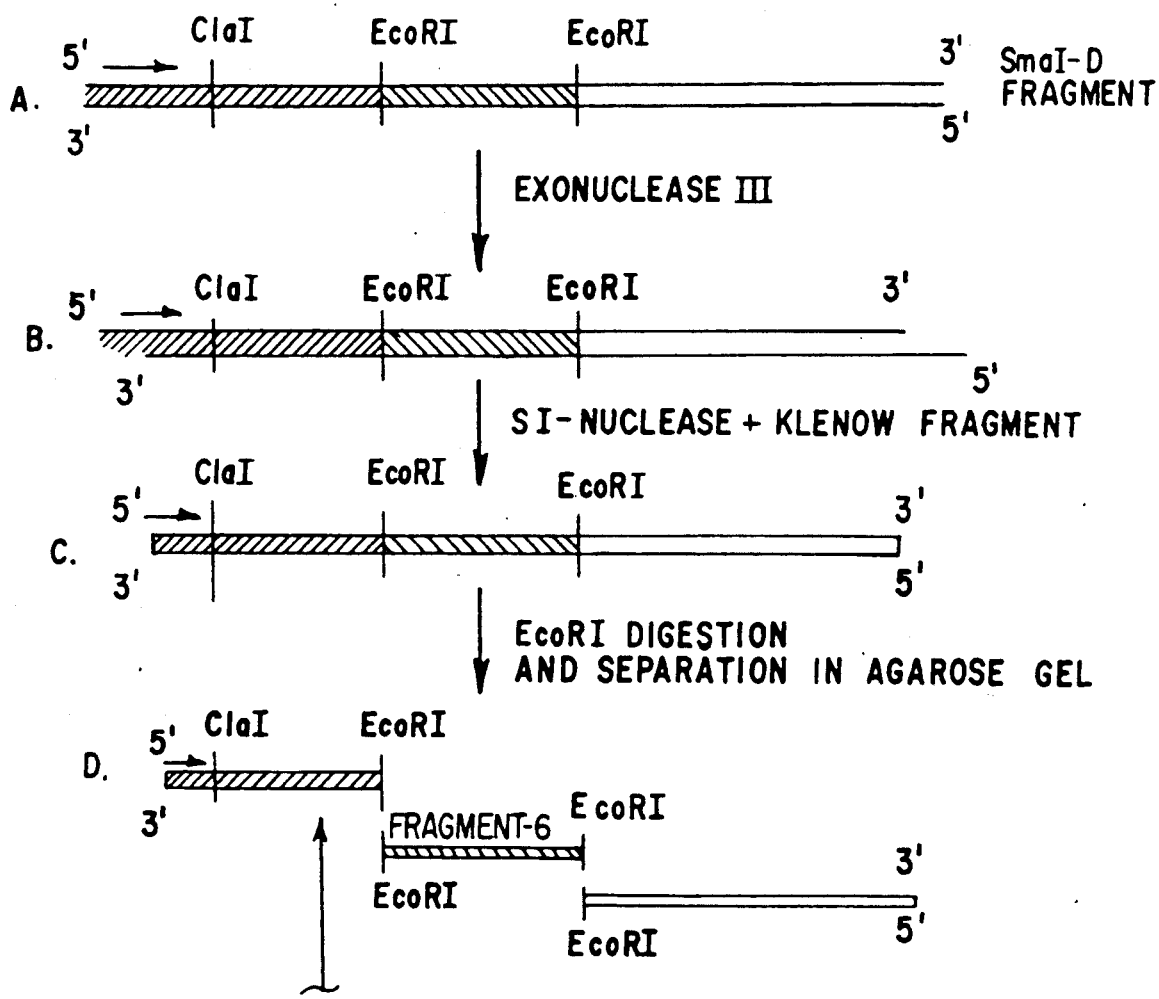
FIG. 2 is a schematic drawing, not necessarily to scale, of many of cloning schemes described in the Examples.
Figure 2:
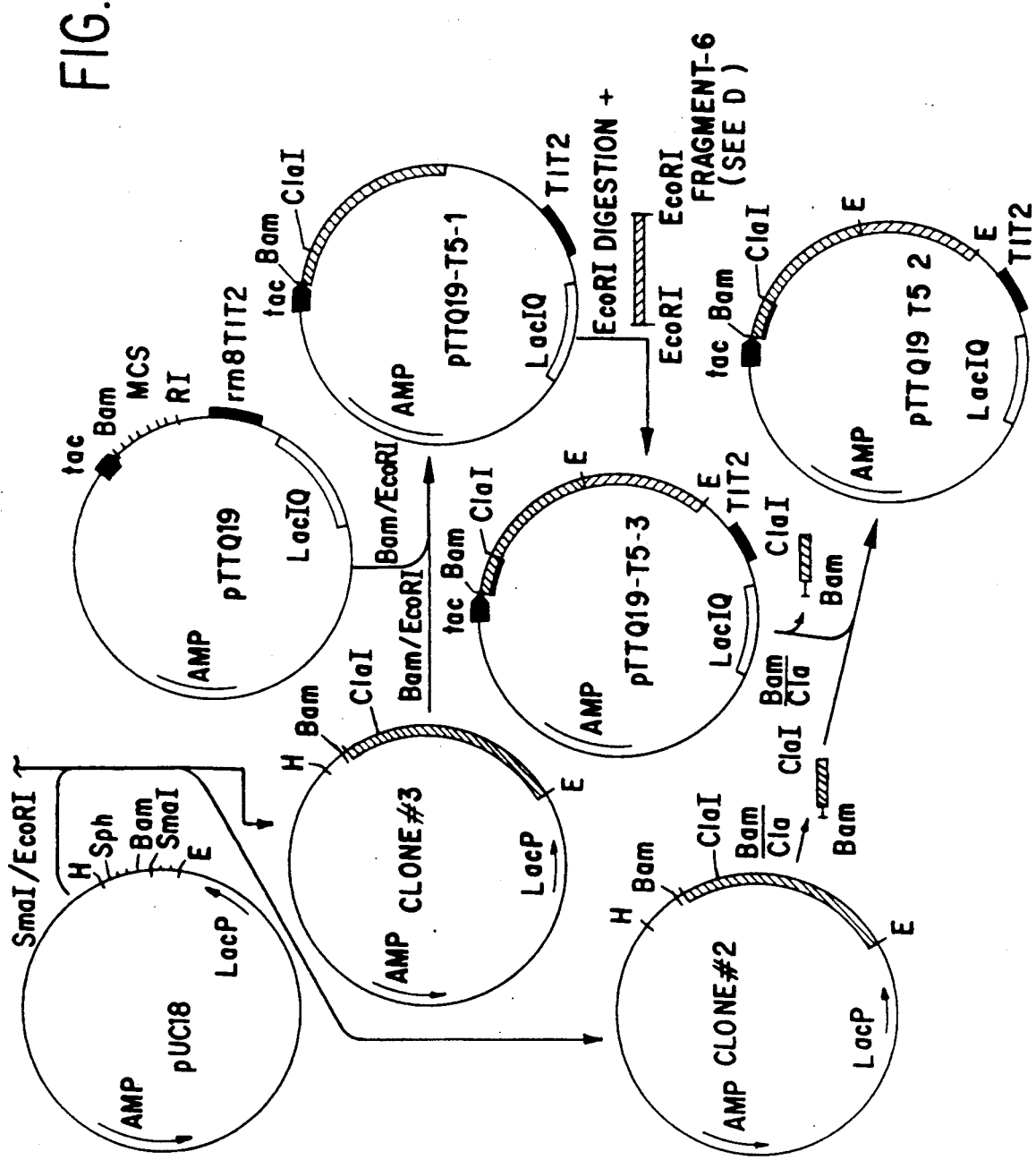

The following terms are defined in order to provide a clear and consistent understanding of their use in the specification and the claims. Other terms are well known to the art so that they need not be defined herein.

"Structural gene" is a term of art referring to that part of a gene that encodes a protein. A gene's translational start and stop codons are included but not the promotor or ribosome binding sites.

"Processive" is a term of art referring to an enzyme's property of acting to synthesize or hydrolyze a polymer without dissociating from the particular polymer molecule. A processive DNA polymerase molecule can add hundreds of nucleotides to a specific nucleic acid molecule before it may dissociate and start to extend another DNA molecule. Conversely, a non-processive polymerase will add as little as a single nucleotide to a primer before dissociating from it and binding to another molecule to be extended. For the purposes of the present invention, processive refers to enzymes that add, on the average, at least 100, and preferably, about 200 or more, nucleotides before dissociation.

"Thioredoxin" is an enzyme well known to the art that is involved in oxidation and reduction reactions. It is also required as a subunit for T7DNA polymerase activity. "Thioredoxin-independent" refers to the ability of an enzymatic activity to be active in the absence of thioredoxin.

"Promoter" is a term of art referring to sequences necessary for transcription. It does not include ribosome binding sites and other sequences primarily involved in translation.

"Heterologous" refers herein to two DNA segments having different origins,; i.e. not, in nature, being genetically or physically linked to each other. Heterologous also describes molecules that are in nature physically or genetically linked together but which are linked together in a substantially different way than is found in nature.

"Homology", as used herein, refers to the comparison of two different nucleic acid sequences. For the present purposes, assessment of homology is as a percentage of identical bases, not including gaps introduced into the sequence to achieve good alignment. Per cent homology may be estimated by nucleic acid hybridization techniques, as is well understood in the art.

"Purifying" refers herein to increasing the specific activity of an enzymatic activity over the level produced in a culture in terms of units of activity per weight of protein. This term does not imply that a protein is purified to homogeneity. Purification schemes for T5-DNAP are know to the art.

The present invention discloses a recombinant DNA molecule having a structural gene encoding a protein, a promoter heterologous to the structural gene, and an origin of replication heterologous to the structural gene.

In this combination the protein has a processive, thioredoxin-independent DNA polymerase activity, the promoter and the structural gene are in such position and orientation with respect to each other that the structural gene may be expressed in a cell under control of the promoter, and the origin of replication is capable of maintaining the promoter/structural gene/origin of replication combination in a cell. Preferably, the promoter and the origin of replication are functional in the same cell, exemplified herein by an $E.$ $coli$ cell. The molecule is preferably contained by cell, exemplified herein by an $E.$ $coli$ cell (in particular, $E.$ $coli$ BH215 (pTTQ19-T5-2), NRRL B-18526), but may, of course, exist in vitro. The promoter may be inducible, e.g. a lambda$_p$L promoter or a tac promoter. The protein may also have a processive 3'-to-5' DNA exonuclease activity. Preferably, the structural gene is not under control of a homologous promoter. In the preferred example, the structural gene is under the control of a heterologous ribosome binding site, not a homologous ribosombinding site.

The structural gene should have at least about 75% homology with T5 DNA polymerase structural gene, and preferably at least about 90% homology, provided that the protein when expressed has T5 DNA polymerase activity. The structural gene may be derived from the T5 DNA polymerase structural gene, and is exemplified herein by the T5 DNA polymerase structural gene. The DNA comprising the T5 DNA polymerase structural gene may be derived from genomic DNA, cDNA, synthetic DNA and combinations thereof.

Alternatively, the structural gene encodes a protein having at least about 75% homology with T5 DNA polymerase, preferably at least about 90% homology, again provided that the protein when expressed has T5 DNA polymerase activity. The structural gene encodes a protein derived from T5 DNA polymerase, and is exemplified herein by a structural gene encoding T5 DNA polymerase. Specific molecules exemplified herein include "clone #2", pTTQ19-T5-2, which is preferred, and derivatives thereof.

The present invention pertains both to the T5 DNA polymerase and to its functional derivatives. A "functional derivative" of T5 DNA polymerase is a compound which possesses a biological activity (either functional or structural) that is substantially similar to a biological activity of T5 DNA polymerase. The term "functional derivative" is intended to include the "fragments," "variants," "analogs," or "chemical derivatives" of a molecule. A "fragment" of a molecule such as T5-DNAP, is meant to refer to any polypeptide subset of the molecule. A "variant" of a molecule such as T5-DNAP is meant to refer to a molecule substantially similar in structure and function to either the entire molecule, or to a fragment thereof. A molecule is said to be "substantially similar" to another molecule if both molecules have substantially similar structures or if both molecules possess a similar biological activity. Thus, provided that two molecules possess a similar activity, they are considered variants as that term is used herein even if the structure of one of the molecules is not found in the other, or if the sequence of amino acid residues is not identical. An "analog" of a molecule such as T5-DNAP is meant to refer to a molecule substantially similar in function to either the entire molecule or to a fragment thereof. As used herein, a molecule is said to be a "chemical derivative" of another molecule when it contains additional chemical moieties not normally a part of the molecule. Such moieties may improve the molecule's solubility, absorption, biological half life, etc.

The present invention also discloses a method for production of a protein having a processive, thioredoxin-independent DNA polymerase activity having the steps of culturing a cell containing a recombinant DNA molecule under conditions were the structural gene is expressed, followed by purifying the protein expressed during the culturing step. In this method, the recombinant DNA molecule has a structural gene encoding the protein, a promoter, and an origin of replication heterologous to the structural gene. The promoter and the structural gene are in such position and orientation with respect to each other that the promoter may be expressed in a cell under control of the promoter. Also, the origin of replication is heterologous to the structural gene and capable of maintaining the structural gene/origin of replication combination in the cell. Expression and maintenance are preferably in an E. coli cell. The promoter may be heterologous to the structural gene and may be inducible, e.g. a lambda$_p$L promoter or a tac promoter. Preferably, the structural gene is not under control of a homologous promoter. In the preferred example, it is not under control of a homologous ribosome-binding site, being under control of a heterologous ribosome binding site. The protein may have a processive 3'-to-5' DNA exonuclease activity. The structural gene should have at least about 75% homology with a T5 DNA polymerase structural gene, and preferably at least about 90% homology. The structural gene should be derived from a T5 DNA polymerase structural gene, and is exemplified herein by a T5 DNA polymerase structural gene. Alternatively, the structural gene encodes a protein having at least about 75% homology with T5 DNA polymerase, preferably at least about 90% homology, provided that the protein when expressed has T5-DNAP activity. The structural gene encodes a protein derived from T5 DNA polymerase, and is exemplified herein by a structural gene encoding T5 DNA polymerase. Specific molecules exemplified herein include "clone #2", pTTQ19-T5-2, which is preferred, and derivatives thereof.

Other promoters, vectors, and host cells, both prokaryotic and eukaryotic, are well known in the art and in keeping with the specification, may be used to practice the invention.

The present invention further discloses a protein having a processive, thioredoxin-independent DNA polymerase activity produced by the method of present invention. This protein may have a processive 3'-to-5' DNA exonuclease activity. The protein should have at least about 75% homology with T5 DNA polymerase, and preferably at least about 90% homology, provided that the T5DNAP has biological activity. The protein may be derived from, and is herein exemplified by, T5 DNA polymerase.

The T5 DNA polymerase of this invention may be used in cloning and expression experiments to produce a heterologous polypeptide from the cloned gene. The T5-DNAP of this invention may also be used for DNA sequencing.

Having now generally described this invention, the same will be better understood by reference to specific examples, which are included herein for purposes of illustration only, and are not intended to be limiting unless otherwise specified.

EXAMPLES

Though the written description that follows is complete and accurate, some may find that overall cloning strategy may be more easily understood by reference to FIG. 2.

EXAMPLE 1:

Isolation of T5 phage DNA

Growth of E. coli and infection with bacteriophage T5 were done as previously described by Schneider SE et al., J. Virol. 56:245–249 (1985).

Purification of T5 phage DNA was isolated by the following procedure. Briefly, E. coli F (provided by Dr. Robert Fujimura, Oak Ridge National Laboratory, Oak Ridge, Tenn.) was grown in Luria broth at 37° C. to an $O.D._550$ of about 0.50. $CaCl_2$ was aided to the final concentration of 2 mM. T5 phage (nickless) (provided by Dr. Fujimura) was added at an approximate cell:phage ratio of 15:0.16. The phage-infected cells were shaken very slowly at 37° C. until the $OD_550$ decreased from about 0.50 to about 0 2. The cells and the cell debris were removed by centrifugation. The supernatant was saved.

To about 900 ml of this supernatant, DNase I and RNase A were added to final concentrations of 10 microg/ml each and $MgCl_2$ was added at a final concentration of 5 mM. The supernatant was then incubated 30 minutes at room temperature. Solid NaCl was added to 1M and dissolved. Then PEG 6000–8000 (PEG=polyethylene glycol) was added to 10% and dissolved. The mixture was incubated overnight at 4° C. The resultant solution of phage was spun for 15 minutes at 6000 rpm; suspended in 50 ml buffer D (buffer D=50 mM Tris♥HCl, pH 7.2, 8.5 mM NaCl, 1 mM $MgCl_2$ and 0.1 mM $CaCl_2$).

A portion (25 ml) was mixed slowly with 20 ml chloroform and then spun for 10 minutes. The aqueous, DNA-containing layer (20 ml) was recovered. SDS (sodium dodecyl sulfate) was aided to this layer to a concentration of 1%. After mixing slowly, this was incubated at 37° C. for 10 minutes. Water-saturated phenol (25 ml) was added, mixed slowly but thoroughly and then spun to separate the layers. The upper, viscous, DNA-containing layer was removed carefully and extracted once again with phenol. Then an equal volume of water-saturated phenol:CHCl$_3$:isoamyl alcohol (50:48:2 v:v:v) was added, mixed slowly and spun to separate the layer. The DNA-containing viscous layer was removed and an equal volume of buffer D was added.

CsCl was added to 1.15 g/ml for purification of the phage DNA by CsCl gradient centrifugation at 40,000 r.p.m. for 2 days. About 9.6 mg of T5 DNA was recovered in 15 ml volume.

EXAMPLE 2:

Exonuclease III and S1 nuclease digestion

Initial attempts to clone an intact fragment containing the polymerase gene met with failure. In addition, smaller fragments containing a portion of polymerase gene (5'-end) and the upstream region also could not be cloned. That suggested that the upstream region of the T5-DNAP gene presence either of very strong (e.g. constitutive) promoter or of some other sequence(s) lethal to E. coli. Therefore, upstream sequences were deleted as follows. A fragment containing entire T5-

DNAP gene was generated by SmaI digestion and isolated (FIG. 2, DNA A.). Terminal sequences were then removed from that fragment by treating with exonuclease III (FIG. 2, DNA B.), which removes a single strand of a DNA duplex, attacking from the 3'-ends, and S1 nuclease, which removed single-stranded ends left after exonuclease III treatment. The ends were "polished" with the Klenow fragment of DNA polymerase I in the presence of all four deoxyribonucleotide triphosphates (FIG. 2, DNA C.). The resulting blunt-ended fragment was then digested with EcoRI to facilitate later cloning (FIG. 2, DNAs D.). The following details the above described steps.

SmaI digestion produces four large fragments, the smallest (about 12 kilobase pairs (kbp)) of which has been suggested (Fujimura R et al., J. Virol. 53:495-500 (1985)) to contain the intact polymerase gene. Therefore, the smallest SmaI fragment was purified from agarose gel with a Gene-Clean(TM) kit (supplied by Bio 101, P.O Box 2284, La Jolla, Calif. 92038-2284 USA).

Exonuclease III (320 units) was added to approximately 2.5 microg DNA in 100 microl of buffer (50 mM Tris HCl, pH 8.0, 10 mM MgCl$_2$ and 1 mM DTT (DTT = dithiothreitol) was kept at 37° C. At various times aliquots were removed. Each aliquot war placed in its own tube containing 200 mM NaCl, 50 mM EDTA .EDTA = ethylenediamine tetraacetic acid). The tubes were then hated at 70° C. for 10 minutes. The DNA contained therein was ethanol precipitated by addition of 0.1 volumes of 3M sodium acetate, pH 6.0, and 2 volumes of ethanol, and incubation in dry ice for 1 to 2 minutes. The DNA precipitate was collected by being spun for 30 minutes at 14,000 r.p.m. in an Eppendorf microfuge.

The exonuclease III digested DNA was dissolved in 50 microl of S1 nuclease buffer consisting of 30 mM sodium acetate, pH 4.6, 50 mM NaCl, 1 mM zinc acetate, and 9 units of S1 nuclease. The reaction was incubated for 30 minutes at room temperature. After extraction with an equal volume of phenol:CHCl$_3$:isoamyl alcohol, the DNA was ethanol precipitated as described above.

The S1 nuclease treated DNA was redissolved in 30 microl of a buffer containing 50 mM potassium phosphate, pH 7.5, 3 mM MgCl$_2$, 2 mM DTT, 0.1 mM each of dATP, dTTP, dGTT, and dCTP, and 1 unit of the Klenow fragment of E. coli DNA polymerase I. The reaction was incubated at room temperature for 5 minutes, extracted with phenol:CHCl$_3$:isoamyl alcohol, and ethanol precipitated as above.

EcoRI cleaves the SmaI fragment isolated above in two places, thereby generating three fragments. The terminally digested SmaI DNA was digested with EcoRI and the resulting DNA fragments were separated by agarose gel electrophoresis and the bands around 2600 base pairs (bp) in size was purified from the agarose gel by Gene-Clean(TM) method. These bands of about 2.6 kbp (kilobase pairs) contain two fragments. One was the central of the three EcoRI sub-fragments of the terminally digested SmaI fragment, the other is the shorter of the two end fragments. This end fragment had its SmaI end trimmed by the exonuclease III/S1 nuclease treatment and had a ClaI site proximal to the "SmaI" end and distal to its EcoRI end. This ClaI site was useful for orienting the fragment, being at the 5'-end of the fragment as defined by the orientation of the T5-DNAP gene.

EXAMPLE 3:

Cloning of a fragment including 5'-flanking sequences

S1 nuclease and Klenow fragment treatment of exonuclease III treated DNA had created a blunt-ended fragment. Later, EcoRI treatment had created a fragment of around 2.6 kbp having a blunt-end on one side (the "SmaI" end, 5'-to the T5-DNAP gene) and sticky EcoRI end on the other. This purified fragment was mixed With and ligated to cloned into pUC18 DNA (Yanisch-Perron C et al. (1985) Gene 33:103-119) which had been previously digested with SmaI and EcoRI. (Note that though the 2.6 kp band contained two different fragments, the 2.6 kbp "end" fragment was preferentially cloned because the internal fragment lacked a blunt end, i.e. its ends did not match those of the vector.) This cloning operation destroyed the SmaI site but preserved the EcoRI site. Six different clones having inserts of varying lengths (but all are around 2.6 kbp) were isolated. One of them, labeled #3, was chosen for further work because this clone contained the largest fragment, i.e the smallest deletion. DNA sequencing showed that the T5 sequences of clone #3 started at nucleotide −98 in the sequence of Leavitt & Ito, supra.

The fragment 3'-to the 2.6 kbp fragment cloned present in clone #3 was placed behind the 2.6 kbp clone #3 fragment. In other words, the 2.6 kbp internal EcoRI fragment was placed ligated to the 2.6 kbp "end" fragment in the orientation which reproduces that found in T5 virus. This was done in an expression vector, pTTQ19 (Stark MJR, Gene 51:255-267 (1987); available from Amersham, International, plc).

pTTQ19 DNA was digested with BamHI and EcoRI and then mixed with and ligated to the 2.6 kbp BamHI/EcoRI fragment of clone #3. The BamHI site was present (in the multiple cloning site (polylinker) of pUC18) next to the SmaI site which had been used to clone the 2.6 kbp fragment of clone #3. The resulting clone was reopened with EcoRI and mixed with and ligated to T5 EcoRI fragment 6 in order to introduce any missing 3'-end (carboxylterminus encoding end) of T5 polymerase gene. (Note that EcoRI fragment 6 can be isolated clean of other T5 sequences, the mixture of two 2.6 kbp fragments was due to an additional cleavage with SmaI.) The resultant clone, pTTQ19-T5-3, produced significant amounts of polymerase activity. Production of T5-DNAP in pTTQ19-T5-3 contained cells was estimated to be over 80-100 fold greater than in phage infected cells.

EXAMPLE 4:

Optimization of the 5'-end of the T5-DNAP gene

Clone #3 was selected from among other clones made at the same time because it had the smallest deletion cf those screened. Sequencing of 5'l-end region of clone #3 and comparison with the published sequence (Leavitt & Ito, supra) showed that the T5 DNA insert of clone #3 carried a promoter-like sequence and a ribosome-binding-site. Therefore, larger deletions were introduced into pTTQ19-T5-3 to see their effect on enzyme production.

The 5'-end of the clone #3 T5 DNA was removed from pTTQ19-T5-3 by digestion with BamHI and ClaI. BamHI/ClaI fragments from independently derived clones, produced in the same experiment that produced clone #3, individually mixed with and ligated to aliquots this DNA. Transformants containing the resultant clones were screened for T5-DNAP production; larger deletion's were observed to produce more enzyme. The clone which produced the highest level of T5-DNAP was estimated by gel electrophoretic analysis to lack all of the presumptive promoter region and the presumptive ribosome binding site. DNA sequencing confirmed that, the 5'-end of the T5 DNA polymerases structural gene is at nucleotide +12, as numbered by Leavitt & Ito, supra. This clone, labeled pTTQ19-T5-2, produced about 4 times more enzymatic activity than pTTQ19-T5-3; cells harboring this plasmid made about 400-fold more units of enzyme than virus-infected cells.

E. coli BH215 (pTTQ19-T5-2) was deposited under the Budapest Treaty with an International Depository Authority, the Patent Culture Collection, Northern Regional Research Center USDA, 1815 N. University St., Peoria, Ill. 61604 U.S.A., as NRRL B-18526. It was accessioned on July 27, 1989, and will be made available to the public upon grant of Letters Patent or publication of this application. Availability of this material is not necessary for practice of the present invention, which may be performed using the teachings of the present disclosure in combination with publicly available materials and information and techniques well known in the arts of molecular biology, recombinant DNA, and chimeric gene expression. This strain is best maintained on Luria broth supplemented with 100 mg/1 ampicillin and 0.2% glucose, to fully repress the tac promoter (see Stark, supra), at 30° C., which lowers the copy number of pUC-based plasmids, thereby lowering the chances of picking up a mutation. This strain may be maintained successfully at 37° C. without supplementary glucose. Protein production is best at 37°.

EXAMPLE 5:

Miscellaneous experiments

Thioredoxin is necessary for production of T5 phage; an E. coli mutant deficient for thioredoxin did not support growth of T5 while an isogeneic strain did. In contrast, active T5-DNAP is made in the deficient strain if it harbors a clone that can express T5-DNAP. Furthermore, addition of thioredoxin in reactions containing T5-DNAP made in a thioredoxin-deficient strain did not affect activity. Therefore, thioredoxin is not an accessory protein to the polymerase and has some other function in the T5 life cycle.

The BamHI/ClaI fragment of clone #3 was subcloned as a BamHi-blunt fragment by treating ClaI digested DNA with klenow fragment and then digesting with BamHI into M13mp18 and M13mp19 at BamHI/SmaI sites, which are identical except for the orientation of their poly-linkers (Yanisch-Perron et al., supra). This fragment, about 650 bp in length, has the pUC18 poly-linker BamHI site at one end and the T5 ClaI site present near the "5'-end" of the 2.6 kbp "end fragment" at the other end. More than 300 times more clones were observed with the M13mp18 ,vector, where the T5 fragments was in the wrong orientation to be transcribed by the lac promoter of the pUC vector, than with M13mp19, where it is the correct orientation. This indicated that a sequence detrimental to E. coli or M13 replication was present on the 650 bp fragment and that its detrimental effects were dependent on being transcribed in the same orientation of the native T5-DNAP gene This is not inconsistent with a need to translate this detrimental sequence. Analysis of expression of deleted variants reported in Example 5 suggests that the detrimental sequence is at the BamHI-end (5'-end) of the fragment. It is likely that this region of the T5-DNAP gene encodes the 3'-to-5' exonuclease activity, thus suggesting that expression of this activity in the absence of the polymerase activity is detrimental to E. coli.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

I claim:

1. An isolated recombinant DNA molecule comprising
   (a) a structural gene encoding a protein, wherein said protein has a T5 DNA polymerase activity,
   (b) a promoter, wherein said promoter and said structural gene are in such position and orientation with respect to each other that said structural gene may be expressed in a cell under control of said promoter, and
   (c) an origin of replication capable of maintaining the promoter/structural gene/origin of replication combination in a cell.

2. A cell containing the molecule as in claim 1, wherein the molecule is contained by a cell.

3. The cell as in claim 2, wherein the cell is an E. coli cell.

4. The molecule as in claim 1, wherein the promoter is inducible.

5. The molecule as in claim 4, wherein the inducible promoter is a lambda$_p$L promoter.

6. The molecule as in claim 4, wherein the inducible promoter is a tac promoter.

7. The molecule as in claim 1, wherein the structural gene encodes a protein having a processive 3'-to-5' DNA exonuclease activity.

8. The molecule as in claim 1, wherein the structural gene is under control of a heterologous promoter.

9. The molecule as in claim 1, wherein the structural gene is under control of a heterologous ribosome-binding site..

10. The molecule as in claim 1, wherein the origin of replication is heterologous to the structural gene.

11. The molecule as in claim 1, wherein the structural gene encodes a functional derivative of a T5 DNA polymerase protein.

12. The molecule as in claim 11, wherein the functional derivative has at least 90% homology with a T5 DNA polymerase protein.

13. The molecule as in claim 11, wherein the functional derivative has at least 75% homology with a T5 DNA polymerase protein.

14. The molecule as in claim 1, wherein the molecule is pTTQ19-T5-3.

15. The molecule as in claim 1, wherein the molecule is pTTQ19T-5-2 or a derivative thereof.

16. A cell containing the molecule of claim 15, wherein the cell is an E. coli BH215 cell.

17. The molecule as in claim 1, wherein the structural gene encodes a protein having T5 DNA polymerase activity synthesizes an average of at least 100 nucleotides before dissociation.

18. The molecule as in claim 17, wherein the T5 DNA polymerase activity synthesizes an average of at least 200 nucleotides before dissociation.

19. A recombinant DNA molecule, wherein the molecule is clone #2 as shown in FIG. 2.

20. A recombinant DNA molecule, wherein the molecule is pTTQ19-T5-1.

* * * * *